United States Patent [19]
Yoon

[11] Patent Number: 5,570,690
[45] Date of Patent: Nov. 5, 1996

[54] IMPLANTABLE DIAGNOSTIC DEVICE FOR INDICATING STRUCTURAL CHANGES OF INTERNAL ANATOMICAL TISSUE AND SYSTEM AND METHODS THEREFOR

[76] Inventor: InBae Yoon, 2101 Highland Ridge Dr., Phoenix, Md. 21131

[21] Appl. No.: 417,068

[22] Filed: Apr. 3, 1995

[51] Int. Cl.$^6$ ...................................................... A61B 5/00
[52] U.S. Cl. .............................................................. 128/630
[58] Field of Search ..................................... 128/630, 778, 128/774, 775, 834, 839, 840; 604/96, 97, 98, 99, 100, 101, 102, 103, 104; 600/29, 30, 31; 607/62, 138

[56] References Cited

U.S. PATENT DOCUMENTS

| | | |
|---|---|---|
| 3,635,223 | 1/1972 | Klieman . |
| 4,222,377 | 9/1980 | Burton ........................................ 600/31 |
| 4,893,623 | 1/1990 | Rosenbluth ............................. 604/104 |
| 5,406,961 | 4/1995 | Artal . |

*Primary Examiner*—George Manuel

[57] ABSTRACT

An indicating device for indicating structural change of internal anatomical tissue includes a bladder for being implanted in the body adjacent internal anatomical tissue and having a variable size passage preventing leakage of a fluidic substance from the bladder when the bladder is initially implanted and causing leakage of the fluidic substance from the bladder when the bladder is stressed in response to structural change of the internal anatomical tissue. A system for indicating structural change of internal anatomical tissue includes a bladder and a penetrating member for penetrating internal anatomical tissue to implant the bladder within the internal anatomical tissue and for supplying a fluidic substance to the bladder once the bladder is implanted in the tissue. A method of indicating structural change of internal anatomical tissue includes the steps of implanting a bladder in the body adjacent internal anatomical tissue, supplying a fluidic substance to the bladder to close a variable size passage of the bladder to prevent leakage of the fluidic substance from the bladder when the bladder is initially implanted and leaving the bladder in the body such that the variable size passage is opened to permit leakage of the fluidic substance from the bladder when the bladder is stressed due to structural change of the internal anatomical tissue.

30 Claims, 3 Drawing Sheets

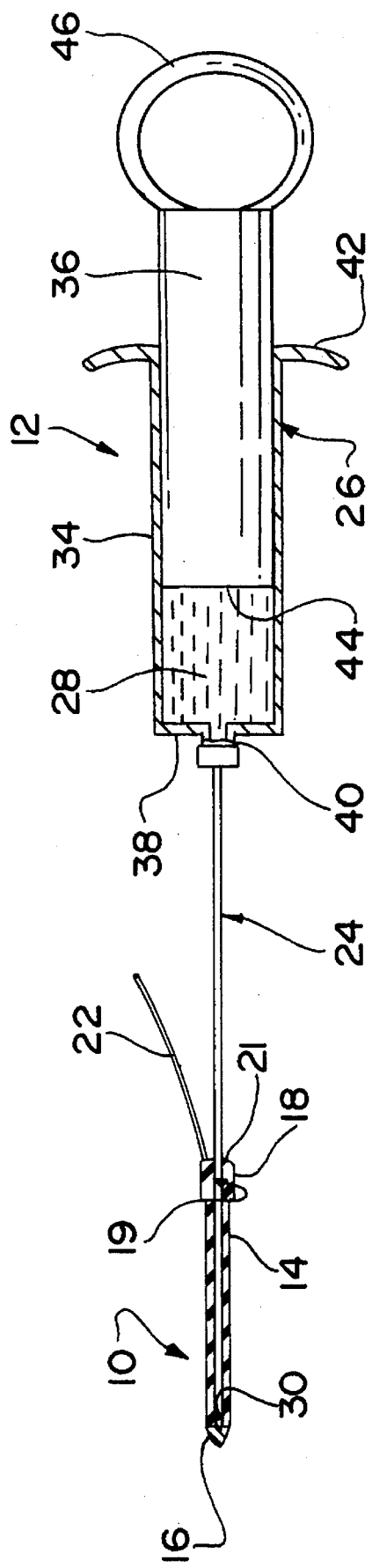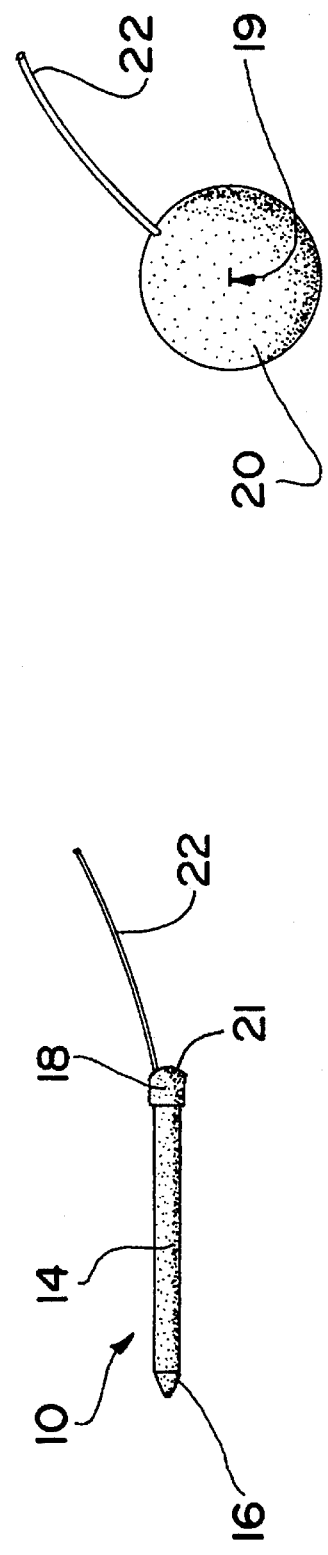

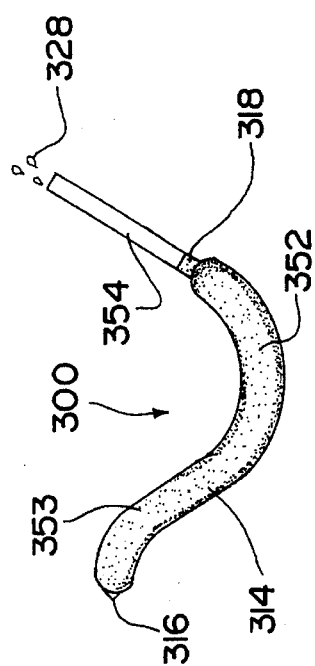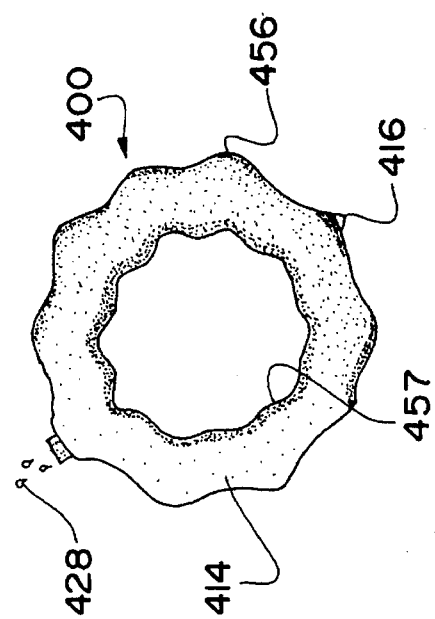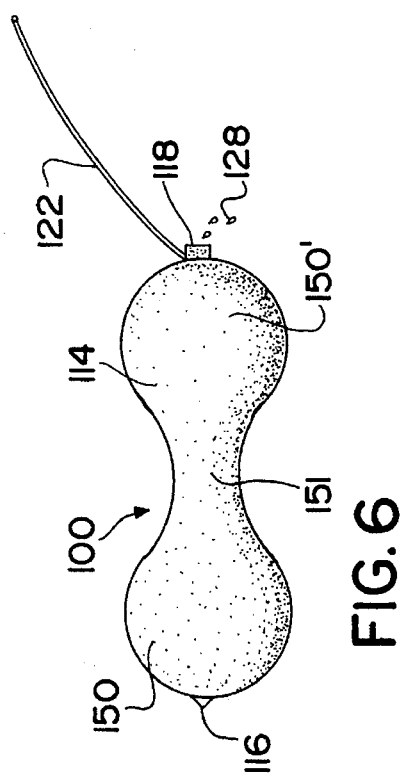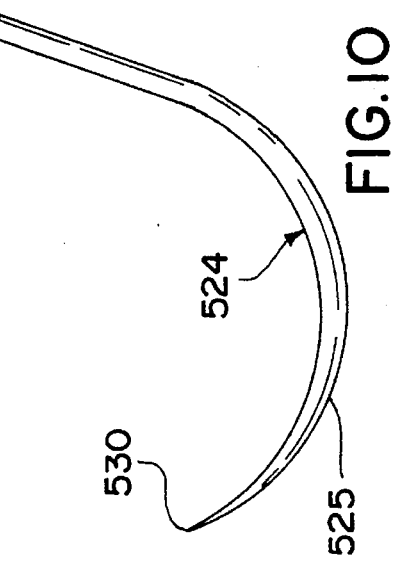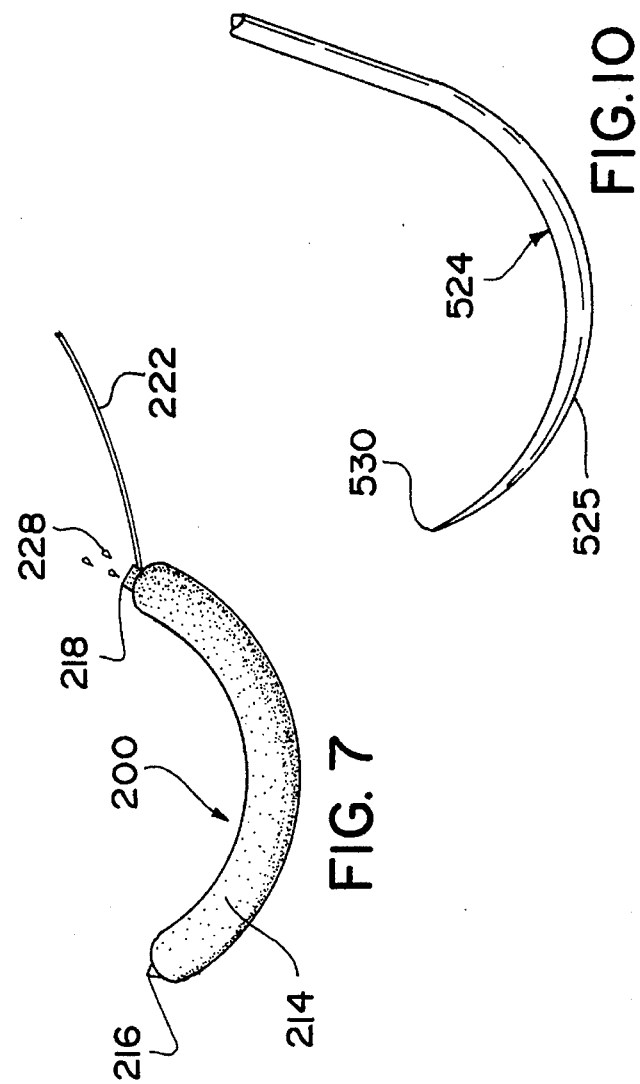

IMPLANTABLE DIAGNOSTIC DEVICE FOR INDICATING STRUCTURAL CHANGES OF INTERNAL ANATOMICAL TISSUE AND SYSTEM AND METHODS THEREFOR

BACKGROUND OF THE INVENTION

1. Field of the Invention

The present invention relates generally to detecting structural changes of internal anatomical tissue and, more particularly, to devices for being implanted in the body to indicate of structural changes of internal anatomical tissue and to systems and methods therefor.

2. Description of the Prior Art

Many various conditions and diseases cause internal anatomical tissue including organ structure to undergo various structural changes such as changes in size, configuration, consistency and density. Many structural changes of internal anatomical tissue are indicative of disease and/or the need for treatment; however, the internal location of the structural changes within the body makes early detection extremely difficult. One area in which structural changes of tissue occurs involves cervical changes during pregnancy. The cervix, which consists primarily of fibrous tissue and smooth muscle, acts as a form of sphincter adaptable in size and shape to accommodate passage of a baby from the uterus into the vagina during childbirth. During pregnancy, the cervix undergoes various changes in preparation for childbirth including cervical effacement wherein the wall forming the cervix thins out and shortens and dilatation wherein the diametric or lateral size of the cervical canal is increased to accommodate passage of the baby.

Many pregnancy patients mistake normal sensations of pregnancy, such as the sensations associated with the baby kicking and moving, for labor pains or contractions. Patients who perceive that they are in labor typically seek medical intervention from physicians and hospitals unnecessarily since they do not know that true labor has not begun. On the other hand, many other pregnancy patients who are in labor may not realize that they are in labor and may fail to timely seek medical attention. The inability of pregnancy patients to detect when cervical changes have occurred and, therefore, to know when labor has begun or is near, gives rise to various communication problems between doctors and patients, increases medical costs and inefficiencies and creates unnecessary patient anxiety.

Occasionally, cervical effacement and dilatation occur prematurely with resulting miscarriage or premature birth. When premature cervical effacement is detected early, preventative measures can be taken to avoid miscarriage and premature delivery and to prolong pregnancy. For example, a suture stitch can be tied like a purse string around the cervix to keep the cervix closed. The suture is left in place until the pregnancy is at or near full term at which time the suture is cut to allow normal delivery of the baby. The success of preventative measures to prolong pregnancy depends on early detection of cervical effacement; however, patients typically do not know when cervical effacement has occurred. Accordingly, such patients may not seek medical attention until after obvious symptoms have occurred, at which time the cervical changes may have progressed to a point where miscarriage or premature delivery cannot be prevented.

Another area in which structural changes of internal tissue occurs involves tumors. In many cases, it is desirable to monitor tumors to detect an increase in size and/or to establish a pattern of growth for diagnostic and/or treatment purposes. Depending on the nature of the tumors or the location of the tumors in the body, monitoring may be difficult and inaccurate even with the use of sophisticated equipment. Additionally, in many instances, changes in tumors are identifiable only with specific medical tests such that significant changes may have already occurred by the time the tests are performed.

Accordingly, there is a great need for a safe, implantable device for indicating structural changes of internal anatomical tissue to allow such changes to be detected as soon as possible after they have occurred.

SUMMARY OF THE INVENTION

Accordingly, it is a primary object of the present invention to indicate structural changes of internal anatomical tissue to allow detection of such changes as soon as possible after they have occurred.

Another object of the present invention is to indicate structural change of internal anatomical tissue with an indicating device implantable in the body and containing a substance having a detectable characteristic released from the indicating device in response to structural change of the anatomical tissue to provide an indication of the structural change.

A further object of the present invention is to indicate structural change of internal anatomical tissue with an indicating device implantable in the body and containing a fluidic substance that is leaked from the indicating device when the indicating device is stressed due to structural change of the anatomical tissue.

An additional object of the present invention is to indicate structural change of internal anatomical tissue externally with a colored substance released from an indicating device implanted in the patient's body and responsive to an increase in pressure on the indicating device caused by structural change of anatomical tissue to release the colored substance for discharge from the patient's body.

The present invention also has as an object to indicate externally the occurrence of cervical effacement with an indicating device implantable in the cervix and sensitive to the occurrence of cervical effacement to release a colored substance into the vagina for discharge from the patient's body.

Yet another object of the present invention is to provide a system for indicating structural change of internal anatomical tissue including a bladder having a variable size passage for closing the bladder and capable of being opened to establish communication with the interior of the bladder and an instrument for implanting the bladder in the body including a penetrating member for being received in the bladder through the variable size passage and a syringe coupled with the penetrating member and containing a fluidic substance, the penetrating member having a distal end for penetrating anatomical tissue to implant the bladder in the tissue and a channel communicating with the syringe to supply the fluidic substance from the syringe to the interior of the bladder such that the variable size passage is closed upon removal of the penetrating member from the bladder to prevent leakage of the fluidic substance from the bladder and is opened when increased pressure is applied to the bladder due to structural change of the anatomical tissue to cause leakage of the fluidic substance from the bladder.

A still further object of the present invention is to provide a method of indicating structural change of internal anatomical tissue comprising the steps of implanting an indicating device including a bladder in the body and supplying a fluidic substance to the bladder to pressurize the bladder such that a variable size passage of the bladder is closed to prevent leakage of the fluidic substance from the bladder when the bladder is implanted and is opened when the bladder is stressed due to structural change of the anatomical tissue to cause the fluidic substance to leak from the bladder.

Some of the advantages of the present invention are that pregnancy patients can distinguish false labor from true labor thusly reducing patient anxiety and improving communication between doctors and patients, cervical problems during pregnancy can be diagnosed early thusly improving the success of preventative measures, tumor growth can be monitored for diagnostic and treatment purposes, the nature and type of structural change of anatomical tissue can be determined in addition to the occurrence of the structural change, staged or sequential monitoring of structural changes of anatomical tissue can be achieved with the use of a plurality of indicating devices and the fluidic substances can have various types of sensible or detectable characteristics in accordance with the nature or type of indication desired.

These and other objects, advantages and benefits are realized with the present invention as characterized in a system for indicating structural change of internal anatomical tissue and including an indicating device and an instrument for implanting the indicating device in the body. The indicating device includes a bladder for being supplied with a fluidic substance and having a variable size passage at a proximal end of the bladder for closing off or sealing the bladder and capable of being opened to establish communication with the interior of the bladder. The bladder is disposed in a non-expanded or collapsed condition prior to being supplied with a fluidic substance and is in an expanded or pressurizxed condition when supplied with a fluidic substance. The instrument for implanting the bladder includes a penetrating member having a distal end for penetrating anatomical tissue and a proximal end and a syringe containing a fluidic substance coupled with the proximal end of the penetrating member. The penetrating member includes a channel or lumen establishing fluid communication between the syringe and the interior of the bladder when the penetrating member is inserted in the bladder through the variable size passage. The syringe includes a housing containing the fluidic substance and a plunger slidably disposed in the housing for ejecting the fluidic substance from the housing and into the channel to be supplied to the bladder.

In uses, the bladder, prior to being supplied with a fluidic substance, is placed over the distal end of the penetrating member as permitted by the penetrating member passing through the variable size passage. The penetrating member with the bladder thereon is utilized to penetrate anatomical tissue to position the bladder in the tissue. Once the bladder is positioned in the tissue, the syringe is squeezed to eject the fluidic substance through the channel of the penetrating member and into the interior of the bladder. The bladder is pressurized with the fluidic substance such that the variable size passage is closed upon removal of the penetrating member from the bladder to prevent leakage of the fluidic substance therefrom. Increased pressure on the bladder caused by structural change of the anatomical tissue causes the variable size passage to open such that some of the fluidic substance is released from the bladder and is detectable or sensible to provide an indication of the structural change.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a side view, partly in section, of a system for indicating structural changes of internal anatomical tissue according to the present invention.

FIG. 2 is a side view of an indicating device of the system of FIG. 1.

FIG. 3 is an end view of the indicating device of FIG. 2.

FIG. 6 is a side view of a modification of an indicating device according to the present invention.

FIG. 7 is a side view of a further modification of an indicating device according to the present invention.

FIG. 8 is a side view of another modification of an indicating device according to the present invention.

FIG. 9 is a top view of yet another modification of an indicating device according to the present invention.

FIG. 10 is a broken side view of a modification of a penetrating member for the system of FIG. 1.

DESCRIPTION OF THE PREFERRED EMBODIMENTS

Figure 5:
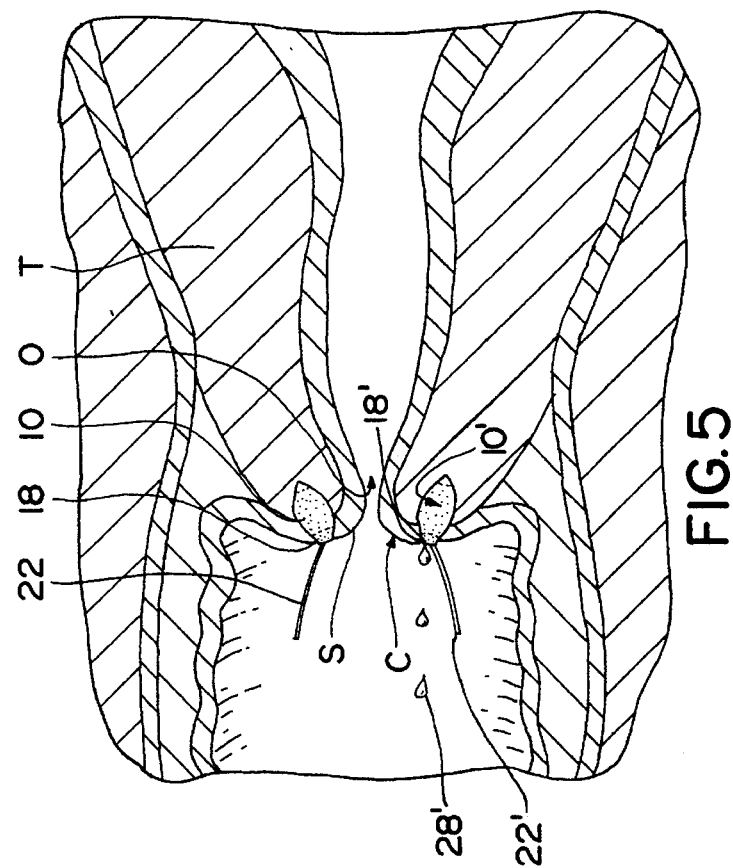
FIG. 5 is a broken frontal view, partly in section, illustrating indication of cervical effacement by the indicating device.

A system for indicating structural changes of internal anatomical tissue according to the present invention is illustrated in FIG. 1 and includes an indicating device 10 and an instrument 12 for implanting the indicating device 10 in the body. The indicating device 10, as best shown in FIGS. 1–3, includes a hollow body or member 14 made of any suitable medical grade material including non-elastic or non-stretchable materials as well as stretchable, expandable, elastic, flexible or resilient materials forming a balloon, bladder, envelope, bag or membrane for holding or retaining a fluidic substance. Bladder 14 has a closed distal end 16 and a thickened proximal portion 18 defining a variable size passage or opening 19. Bladder 14 can have any desirable configuration in accordance with procedural use; and, as shown in FIGS. 1 and 2, bladder 14 has an elongate cylindrical configuration with a tapered, pointed or conical distal end 16. Bladder 14 is disposed in a non-expanded or collapsed position or condition prior to a fluidic substance being supplied to the bladder and in an expanded or pressurized position or condition when a fluidic substance is supplied to the interior of the bladder as explained further below. The distal end 16 is of increased hardness, strength or rigidity or is reinforced to prevent penetration therethrough by a distal end of a penetrating member of instrument 12 as explained further below. Distal end 16 preferably has a configuration to cooperate with or correspond to the configuration of the penetrating member distal end to facilitate penetration of anatomical tissue as explained below. The distal end 16 can be formed or treated in many various ways to prevent penetration therethrough by the penetrating member. The distal end 16 can be made separately from and/or of a different material than the remainder of bladder 14, or the distal end 16 can be made integrally, unitarily with and/or of the same material as the remainder of bladder 14. As best shown in FIGS. 1 and 3, the tubular wall of bladder 14 is of increased thickness in a radial direction to define thickened proximal portion 18 which forms a stretchable, elastomeric seal 20 at a proximal end 21 of bladder 14 such that the variable size passage 19 is normally closed as shown in FIG. 3 to close off or seal bladder 14. The proximal end 21 can have a rounded configuration as shown presenting no sharp edges or corners when the indicating device 10 is implanted in the body as explained below. A withdrawal string 22 can be attached to the proximal portion 18 to facilitate withdrawal of the indicating device 10 from the body as explained further below; however, the indicating device 10 need not have a withdrawal string depending on procedure and/or area of use. The instrument 12 includes an elongate penetrating member 24 and a syringe 26 coupled with penetrating member 24 and containing a fluidic substance 28. Penetrating member 24 includes a distal end 30 for penetrating anatomical tissue and a proximal end coupled to syringe 26. The distal end 30 can have any desirable configuration to penetrate tissue to implant the indicating device 10 therein; and, as shown in FIG. 1, the distal end 30 has an angled configuration tapering to a sharp tip cooperating with the tapered configuration of the distal end 16 of bladder 14. The penetrating member 24 is hollow or cannulated to define an internal passage, channel or lumen with the distal end 30 being open to allow the fluidic substance 28 to be ejected from the syringe and supplied to bladder 14 through the lumen and the open distal end 30 of the penetrating member as explained below. However, the penetrating member can be solid or partly solid and formed with an internal or external passage or channel therealong communicating with syringe 26 for supplying the indicating device 10 with the fluidic substance 28.

Syringe 26 includes a housing 34 containing fluidic substance 28 and a cylindrical plunger 36 slidably disposed in housing 34. Housing 34 includes a forward or distal end wall 38 having an aperture therein and a tubular neck 40 protruding distally from forward wall 38 in alignment with the aperture therein for receiving the proximal end of the penetrating member 24. The penetrating member 24 can be non-removably coupled with the housing 34, such as by being formed unitarily, integrally with the syringe 26, or the penetrating member 24 can be removably coupled with the housing 34 such as with the use of a threaded connection or various other releasable detent mechanisms. The housing 34 has an open rearward or proximal end including a distally curved annular flange 42. The plunger 36 is slidably disposed within the housing 34 through the open rearward end thereof with the fluidic substance 28 being confined between the housing forward wall 38 and a forward end 44 of plunger 36. Plunger 36 includes a rearward end disposed externally of housing 34 and provided with a thumb ring handle 46 allowing the housing 34 and the plunger 36 to be grasped with one hand to slide or depress the plunger within the housing to eject fluidic substance 28. The fluidic substance 28 includes a fluid having a characteristic that can be sensed or whose presence can be tested for. In the case of the indicating system of FIG. 1, fluidic substance 28 is a colored, medical-grade or biocompatible dye such as methylene blue. If desired, a seal can be provided at the forward end of housing 34 to prevent leakage of the fluidic substance 28 therefrom until the plunger 36 is depressed.

The indicating device 10 is normally supplied as shown in FIG. 2 in the non-expanded or collapsed position with no fluid supplied to bladder 14 and with the variable size passage 19 closed. When it is desired to implant the indicating device 10 in the body, the bladder 14 is assembled or placed over the penetrating member 24 as permitted by stretching or movement of the elastomeric seal 20 to an open position to receive or accomodate the penetrating member when the penetrating member 24 is passed through the variable size passage 19 into the interior of bladder 14. With the penetrating member 24 fully inserted in the bladder 14 as shown in FIG. 1, the distal end 30 of the penetrating member 24 will be disposed within or aligned with the distal end 16 of the bladder 14 such that the distal end of the bladder and the distal end of the penetrating member together form a tissue penetrating tip.

Figure 4:
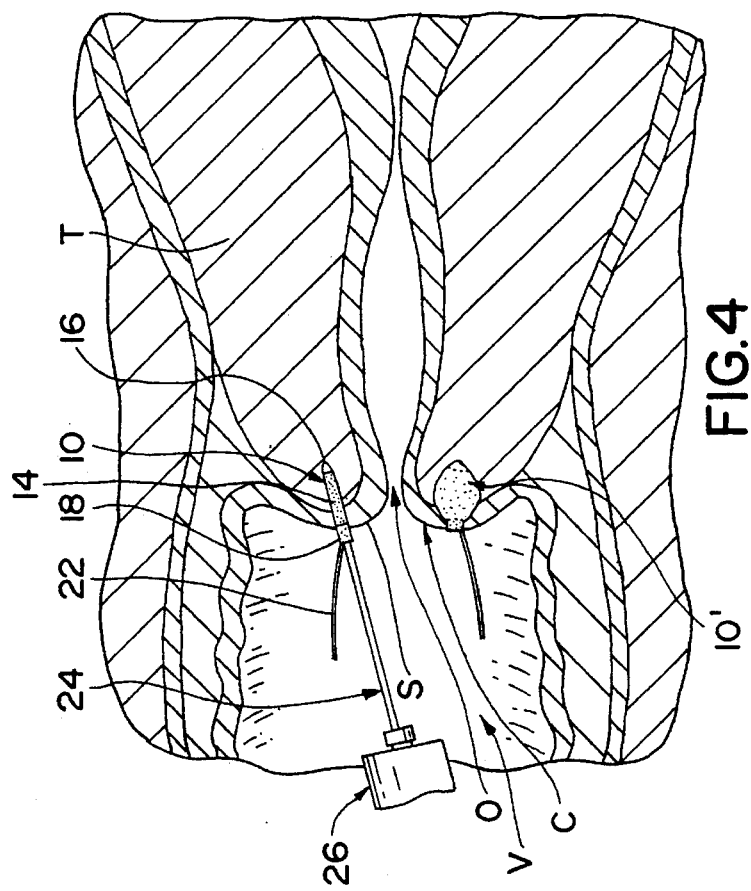
FIG. 4 is a broken frontal view, partly in section, illustrating implantation of the indicating device in the cervix.

FIGS. 4 and 5 illustrate use of the indicating system of FIG. 1 to indicate cervical effacement. The syringe 26 is held via the flange 42 and the ring handle 46, and the penetrating member 24 with the bladder 14 disposed thereon in the non-expanded position is inserted into the vaginal canal. The tissue penetrating tip formed by the distal end 16 of the bladder 14 as reinforced by the distal end 30 of the penetrating member 24 is utilized to penetrate the tissue T of the cervix C adjacent the external cervical os O as shown in FIG. 4. The indicating device 10 is inserted in the tissue T until the proximal end 21 is flush with or protrudes from the external tissue surface S with the withdrawal string 22 protruding therefrom to facilitate withdrawal of the indicating device 10. Once the indicating device 10 has been inserted in the tissue T to the proper depth, the syringe 26 is squeezed thusly depressing plunger 36 into the housing 34. Accordingly, the fluidic substance 28 will be ejected from the housing 34 and through the lumen of the penetrating member 24 into the interior of bladder 14 to move the bladder from the non-expanded position to an expanded pressurized position or condition. The amount or quantity of fluidic substance 28 supplied to the bladder 14 to pressurize the indicating device 10 is selected by the surgeon in accordance with a desired predetermined pressure, and the bladder 14 can be expanded to different sizes. The predetermined pressure for the indicating device 10 when initially implanted is determined by the surgeon from various factors including structural characteristics of the cervix, the stage of effacement for which indication is desired and characteristics of the patient including weight, the position of the baby and history of prior birth. The predetermined pressure is selected to cause the seal 20 to close upon withdrawal of penetrating member 24 from bladder 14 and to remain closed until structural changes of the cervix C causes the tissue T to exert increased pressure on or to stress the indicating device 10. Once the indicating device 10 has been pressurized to the desired pressure, the penetrating member 24 is withdrawn from the bladder 14 and the instrument 12 is removed from the body leaving the indicating device in place in the tissue. Upon withdrawal of the penetrating member 24, the seal 20 will automatically close or self-seal to close the variable size passage 19 and prevent leakage of the fluidic substance 28 from the indicating device 10. When cervical effacement occurs, the cervix C thins out and shortens, causing tissue T to exert an increased pressure on the indicating device 10. Once the pressure exerted by tissue T on indicating device 10 overcomes the sealing force of seal 20 and causes the variable size passage 19 to open, some of the fluidic substance 28 will leak from the indicating device through the variable size passage as shown in FIG. 5 for indicating device 10. The leakage will be discharged through the vagina; and upon the appearance of a blue vaginal discharge, the patient will know that cervical effacement has occurred. By selecting the predetermined pressure to cause the sealing force to be overcome upon the occurrence of a specific degree of cervical effacement, the degree of effacement that has occurred upon detection of the colored vaginal discharge will also be known.

As shown in FIGS. 4 and 5, more than one indicating device can be implanted in the body for staged or sequential indication of structural changes of internal anatomical tissue. FIG. 4 illustrates a second indicating device 10' implanted in tissue T forming cervix C. Indicating device 10' is pressurized at implantation to a predetermined pressure greater than the pressure to which indicating device 10 is pressurized. Indicating device 10' will be stressed upon the occurrence of cervical effacement to a first predetermined extent or degree, for example, 10% effacement. Accordingly, fluidic substance 28' will be released from indicating device 10' to indicate 10% cervical effacement. Indicating device 10 will be stressed upon the occurrence of cervical effacement to a second predetermined extent or degree, for example, 30% effacement. Accordingly, fluidic substance 28 will be released from indicating device 10 to indicate 30% effacement. Where more than one indicating device is utilized, the indicating devices can be provided with fluidic substances having different characteristics, respectively. For example, the fluidic substance 28 for indicating device 10 can be blue in color whereas the fluidic substance 28' for indicating device 10' can be a second, different color. Where utilized to indicate cervical effacement, it is desired that the fluidic substance not be red in color to avoid confusion with blood.

FIGS. 6–9 illustrate various modifications of indicating devices according to the present invention. FIG. 6 illustrates an indicating device 100 including a bladder 114 which, when supplied with a fluidic substance 128, has a dumbbell-shaped or peanut-shaped external configuration defined by a pair of rounded end sections or protuberances 150 and 150', respectively, and a reduced width or narrowed intermediate section 151 disposed between the end sections 150 and 150'. End section 150 terminates distally at rigidified distal end 116, and end section 150' terminates proximally at thickened portion 118 defining a variable size passage that is closed to prevent leakage of the fluidic substance 128 from the bladder 114 at implantation and is opened to cause leakage of the fluidic substance from bladder 114 as shown in FIG. 6 when the indicating device 100 is stressed due to structural change of tissue. A withdrawal string 122 is attached to the thickened portion 118 to facilitate withdrawal of the indicating device 110 from the body.

An indicating device 200 is illustrated in FIG. 7 and includes a bladder 214 having a circular configuration in cross-section and a curved, arcuate or semi-circular external shape or configuration in the expanded position when pressurized with fluidic substance 228. Bladder 214 has a tearing-resistant distal end 216 and a thickened proximal portion 218 defining a variable sized passage through which fluidic substance 228 is released when increased pressure is exerted on the indicating device 200.

An indicating device 300 is illustrated in FIG. 8 and includes a bladder 314 having a circular configuration in cross-section and a reverse curve or S-shaped external configuration when supplied with fluidic substance 328 in an expanded position. Accordingly, indicating device 300 in the expanded position has an external configuration defined by a proximal curved section 352 and a distal curved section 353 joined to the proximal curved section and curving in a direction opposite the direction of curvature of proximal curved section 352. Distal curved section 353 terminates distally at hard distal end 316, and proximal curved section 352 terminates proximally at thickened proximal portion 318. A tube 354 is attached to the proximal portion 318 to communicate with the variable size passage; and, accordingly, fluidic substance 328 is released through tube 354 when stress is exerted on the indicating device 300. Depending on the area of use, the indicating device 300 can be implanted in the body with the tube 354 exiting the body through a natural or artificial opening to allow external detection of fluidic substance 328 leaked from bladder 314. Tube 354 can have an open tubular construction and can be formed separately from thickened portion 318 or integrally, unitarily therewith. Tube 354 can also be formed as an extension of thickened portion 318 to define a self-sealing variable size passage along the length of tube 354, which passage will open when stress is exerted on the indicating device 300 to allow leakage of fluidic substance 328 from the tube 354. Where indicating device is implanted with an instrument, such as instrument 12, the penetrating member can be inserted into the interior of bladder 314 via the tube 354.

FIG. 9 illustrates an indicating device 400 including a bladder 414 having an annular or ring-like external shape in an expanded position when supplied with fluidic substance 428. In addition, bladder 414 in the expanded position defines an irregular external surface 456 and an irregular internal surface 457 to resist undesired displacement, migration, movement or slippage of the indicating device 410 once the indicating device 410 has been implanted in anatomical tissue. The irregular surfaces can be formed in many various ways, the external and internal surfaces, 456 and 457, respectively, being formed with a wavy, bumpy or corrugated shape. Bladder 414 terminates distally at strengthened distal end 416 and proximally at thickened portion 418 defining a variable size passage through which fluidic substance 428 is leaked when stress is applied to the indicating device 400. The indicating device 400 is provided without a withdrawal string or tube.

The indicating devices illustrated in FIGS. 6–9 present various configurations which may be advantageous for specific uses. For example, when indicating device 400 is implanted in the cervix to surround the cervical os, cervical effacement will be detected over an increased area. Additionally, the various configurations of indicating devices can be useful to fit around various organ or other tissue structures.

A modification of a penetrating member for the instrument 12 is illustrated at 524 in FIG. 10. The penetrating member 524 is particularly useful for implanting curved indicating devices, such as indicating device 200, and includes a hollow needle having a curved distal portion 525 terminating distally at a tapered distal end 530 for penetrating anatomical tissue.

It should be appreciated that the indicating devices and systems can be used in many areas of the body to indicate structural changes of internal anatomical tissue including the stomach, the intestines, the lungs and muscles. Accordingly, it should be appreciated that "internal anatomical tissue" as used herein comprises organ structure and other types of anatomical tissue including healthy tissue and diseased tissue as well as tumors and malignancies. For example, another area of use for the indicating devices of the present invention involves the monitoring of tumors. One or more indicating devices can be implanted within a tumor, next to a tumor, beneath the surface of a tumor or can be attached to a tumor. When initially implanted, the indicating device will be at a predetermined pressure to cause the variable size passage to remain closed to prevent leakage of the fluidic substance from the indicating device. As the tumor grows, increased pressure will be exerted on the indicating device due to the increased size of the tumor and/or due to structural change in the tissue surrounding the tumor. Accordingly, the variable size passage will open causing leakage of some of the fluidic substance. Depending on the location of the indicating device in the body, leakage can be excreted from the body naturally for external detection. For instance, where the indicating device is implanted in the stomach or intestines, leakage from the indicating device will appear in the patient's stool allowing external visual detection. The indicating devices thusly allow tumor growth to be monitored and detected; and, by deploying the indicating devices at implantation to respond to a specific amount or degree of inceased stress or pressure, the rate of tumor growth can be determined. Knowing the rate of tumor growth is of great value to physicians since a pattern of rapid growth is frequently indicative of malignancy.

Depending upon procedure and/or area of use, the indicating devices can be implanted within the tissue, in abutment with the tissue, between layers of the tissue or attached to the tissue. Where utilized to indicate cervical effacement, it is preferable that the indicating devices be implanted in smooth muscle, and the indicating devices can be implanted parallel with the cervical canal, at an angle with the cervical canal or laterally or transversely to the cervical canal depending on the shape of the cervix and the optimum site for implantation as determined by the surgeon. The optimum site for implantation of the indicating devices in the cervix will be determined by the surgeon in accordance with various patient factors, and the optimum site can be anterior, posterior or at any other location determined by the surgeon as providing the most accurate indication of cervical effacement. Where utilized to indicate structural changes associated with tumors, the indicating device can be implanted within the tumor, in the tissue next to the tumor, in abutment with the tumor, attached to the tumor or injected beneath the surface of the tumor.

The predetermined pressure of the indicating devices at implantation should be selected to prevent leakage of the fluidic substance due to incidental stress on the bladder, such as from the baby kicking or false labor in the case of cervical use during pregnancy, so that the fluidic substance is not released until actual effacement or structural change has occurred. The wall thickness of the bladder can be varied in accordance with the degree of sensitivity desired for the indicating devices. The elastomeric seal can be designed in many various ways with a specific sealing force to prevent leakage of the fluidic substance from the bladder when pressurized to a predetermined pressure at implantation and to cause leakage of the fluidic substance from the bladder in response to a predetermined increased pressure or stress exerted on the indicating device. Accordingly, not only can the occurrence of structural change of internal tissue be indicated by the indicating devices but also the nature or extent of the structural change. The indicating devices can have various configurations and sizes depending on area of use, and can be implanted in many various ways in addition to the instrument shown. The indicating devices can be implanted under direct vision or with the use of a remote visualization device. For example, the instrument 12 can be introduced in the body via an operating channel of an endoscope for implantation of the indicating device under endoscopic visualization. Where a penetrating member is utilized for implantation, the penetrating member can have various straight or non-straight configurations in accordance with the configuration of the indicating devices. The indicating devices can be provided with or without a withdrawal string or tube; and, where provided without a withdrawal string or tube, the indicating devices can be implanted with the proximal portion protruding slightly from the external surface of the tissue to facilitate withdrawal of the indicating device. Where the indicating devices are provided with tubes, the tubes can be deployed to exit the body through a natural or artificially created opening, or the tubes can be positioned within the body in communication with an internal cavity from which the leakage can be released externally or excreted. It should also be appreciated, however, that the fluidic substances released from the indicating devices can remain in the body for detection. For example, the fluidic substances can contain a material detectable radiographically upon release from the indicating devices. The fluidic substances can have various characteristics other than or in addition to color to provide an indication of structural change of tissue. For instance, depending on area of use, the fluidic substances can contain a material whose presence can be tested for, such as via blood tests when the fluidic substance is released into the bloodstream. Where a medically acceptable dye such as methylene blue is utilized as the fluidic substance, the dye itself may have antiseptic properties providing therapeutic benefits. The fluidic substances can contain an anesthetic or other therapeutic agents. Where color is utilized in the fluidic substance to indicate structural change, the color or dye can be concentrated to ensure detectability even if mixed with or diluted by bodily fluids.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A device for indicating structural change of internal anatomical tissue comprising
   a bladder for being implanted in the body adjacent the internal anatomical tissue;
   a fluidic substance contained in said bladder and having a detectable characteristic; and
   a variable size, elastomeric passage in said bladder creating a seal preventing leakage of said fluidic substance from said bladder when said bladder is initially implanted adjacent the anatomical tissue and causing leakage of said fluidic substance from said bladder through said variable size passage when said bladder is stressed due to structural change of the anatomical tissue to provide an indication of the structural change.

2. A device for indicating structural change of internal anatomical tissue as recited in claim 1 wherein said fluidic substance includes a biocompatible dye and said detectable characteristic includes a color.

3. A device for indicating structural change of internal anatomical tissue as recited in claim 1 wherein said bladder is pressurized by said fluidic substance to a predetermined pressure when said bladder is initially implanted adjacent the anatomical tissue to cause leakage of said fluidic substance from said bladder in response to a predetermined increased stress on said bladder corresponding to a specific structural change of the anatomical tissue.

4. A device for indicating structural change of internal anatomical tissue as recited in claim 3 wherein said bladder includes a balloon pressurizable to different sizes.

5. A device for indicating structural change of internal anatomical tissue as recited in claim 4 wherein said variable size passage is formed by a thickened, tubular proximal portion of said balloon.

6. A device for indicating structural change of internal anatomical tissue as recited in claim 5 and further including a tube communicating with said variable size passage and into which said fluidic substance is released upon leakage from said bladder.

7. A device for indicating structural change of internal anatomical tissue as recited in claim 6 wherein said tube is formed integrally, unitarily with said thickened, tubular proximal portion and said variable size passage is defined along the length of said tube.

8. A device for indicating structural change of internal anatomical tissue comprising
- a bladder for being implanted in the body adjacent the internal anatomical tissue;
- a fluidic substance contained in said bladder and having a detectable characteristic;
- a variable size passage in said bladder creating a seal preventing leakage of said fluidic substance from said bladder when said bladder is initially implanted adjacent the anatomical tissue and causing leakage of said fluidic substance from said bladder through said variable size passage when said bladder is stressed due to structural change of the anatomical tissue to provide an indication of the structural change; and
- a withdrawal string attached to said bladder to facilitate withdrawal of said bladder from adjacent the anatomical tissue.

9. A device for indicating structural change of internal anatomical tissue comprising
- a bladder for being implanted within internal anatomical tissue having an outer surface;
- a fluid contained within said bladder and having a detectable characteristic; and
- a variable size, self-closing opening integrally, unitarily formed in said bladder for being positioned along the outer surface of the tissue when said bladder is implanted in the tissue, said variable size opening being closed when said bladder is initially implanted in the tissue to prevent communication with the interior of said bladder from externally of the outer surface such that release of said fluid from said bladder is prevented and being opened to establish communication between the interior of said bladder and externally of the outer surface such that some of said fluid in said bladder is released externally of the outer surface when structural change of the tissue causes increased pressure to be exerted on said bladder.

10. A device for indicating structural change of internal anatomical tissue as recited in claim 9 wherein said variable size opening is flush with the outer surface of the tissue when said bladder is implanted.

11. A device for indicating structural change of internal anatomical tissue as recited in claim 9 wherein said variable size opening protrudes beyond the outer surface of the tissue when said bladder is implanted.

12. A device for indicating structural change of internal anatomical tissue as recited in claim 9 wherein said bladder has a non-circular cross-sectional configuration.

13. A device for indicating structural change of internal anatomical tissue as recited in claim 12 wherein said bladder has a dumbbell-shaped external configuration.

14. A device for indicating structural change of internal anatomical tissue as recited in claim 9 wherein said bladder has a circular cross-sectional configuration.

15. A device for indicating structural change of internal anatomical tissue as recited in claim 14 wherein said bladder has a cylindrical external configuration.

16. A device for indicating structural change of internal anatomical tissue as recited in claim 14 wherein said bladder has a semi-circular external configuration.

17. A device for indicating structural change of internal anatomical tissue as recited in claim 14 wherein said bladder has a reverse curved external configuration.

18. A device for indicating structural change of internal anatomical tissue as recited in claim 9 wherein said bladder has an annular external configuration.

19. A device for indicating structural change of internal anatomical tissue as recited in claim 9 wherein said bladder has an external surface and said external surface has an irregular configuration to avoid displacement of said bladder when implanted in the tissue.

20. A system for indicating structural change of internal anatomical tissue comprising
- a bladder for being implanted in the body adjacent internal anatomical tissue and having a variable size passage normally closed to seal said bladder and capable of being opened to establish communication with the interior of said bladder, said bladder being in a collapsed condition prior to a fluidic substance being supplied to said bladder and being in an expanded, pressurized condition when a fluidic substance is supplied to said bladder; and
- an instrument for implanting said bladder in the body adjacent the internal anatomical tissue and including a penetrating member for being inserted in said bladder through said variable size passage, said penetrating member having a distal end for penetrating anatomical tissue to introduce said bladder in the body adjacent the internal anatomical tissue with said bladder in said collapsed condition and having a passage therethrough for supplying a fluidic substance to the interior of said bladder with said penetrating member inserted through said variable size passage, said penetrating member being withdrawable from said bladder through said opening to leave said bladder in the body after said fluidic substance has been supplied to said bladder, said fluidic substance supplied to said bladder causing said bladder to be pressurized in said expanded, pressurized condition to allow said variable size passage to close to prevent leakage of said fluidic substance from said bladder when said bladder is initially left in the body, said variable size passage being opened to cause leakage of said fluidic substance from said bladder when increased pressure is exerted on said bladder from structural change of the internal anatomical tissue.

21. A system for indicating structural change of internal anatomical tissue comprising
- a bladder for being implanted in the body adjacent internal anatomical tissue and having a variable size passage normally closed to seal said bladder and capable of being opened to establish communication with the interior of said bladder, said bladder being in a collapsed condition prior to a fluidic substance being supplied to said bladder and being in an expanded, pressurized condition when a fluidic substance is supplied to said bladder; and
- an instrument for implanting said bladder in the body adjacent the internal anatomical tissue and including a penetrating member for being inserted in said bladder through said variable size passage and a device coupled with said penetrating member for supplying a fluidic substance to the interior of said bladder with said penetrating member inserted through said variable size passage, said penetrating member having a distal end for penetrating anatomical tissue to implant said bladder in the body adjacent the internal anatomical tissue with said bladder in said collapsed condition, said bladder including a distal end for receiving said distal end of said penetrating member when said penetrating member is inserted in said bladder, said distal end of said bladder being rigidified to prevent penetration therethrough by said distal end of said penetrating member when penetrating anatomical tissue, said penetrating member being withdrawable from said bladder through said opening after said fluidic substance has been supplied to said bladder, said fluidic substance supplied to said bladder causing said bladder to be pressurized in said expanded, pressurized condition to allow said variable size passage to close to prevent leakage of said fluidic substance from said bladder when said bladder is initially implanted, said variable size passage being opened to cause leakage of said fluidic substance from said bladder when increased pressure is exerted on said bladder from structural change of the internal anatomical tissue.

22. A system for indicating structural change of internal anatomical tissue as recited in claim 21 wherein said device includes a syringe containing said fluidic substance and a channel extending along said penetrating member.

23. A system for indicating structural change of internal anatomical tissue as recited in claim 22 wherein said distal end of said penetrating member is open and said penetrating member includes a hollow needle having a lumen defining said channel.

24. A system for indicating structural change of internal anatomical tissue as recited in claim 23 wherein said distal end of said needle has a curved configuration.

25. A system for indicating structural change of internal anatomical tissue as recited in claim 21 wherein said bladder includes a tubular proximal end having a radially thickened wall defining said variable size passage.

26. A method of indicating structural change of internal anatomical tissue comprising the steps of providing a bladder having a variable size passage therein movable between a closed position sealing the bladder and an open position providing communication with the interior of the bladder;

implanting the bladder in the body adjacent internal anatomical tissue;

supplying a fluidic substance to the interior of the bladder to pressurize the bladder to cause the variable size passage to be in the closed position preventing leakage of the fluidic substance from the bladder when the bladder is initially implanted in the body and to move to the open position to cause some of the fluidic substance to leak from the bladder when the bladder is stressed in response to structural change of the internal anatomical tissue; and leaving the bladder in the body such that leakage of the fluidic substance therefrom provides an indication of the structural change of the internal anatomical tissue.

27. A method of indicating structural change of internal anatomical tissue as recited in claim 26 and further including the step of providing an instrument for implanting the bladder in the body including a penetrating member having a distal end for penetrating the anatomical tissue and wherein said implanting step includes inserting the distal end of the penetrating member in the bladder through the variable size passage and penetrating the anatomical tissue with the distal end of the penetrating member to position the bladder within the anatomical tissue.

28. A method of indicating structural change of internal anatomical tissue as recited in claim 27 wherein said step of leaving includes withdrawing the distal end of the penetrating member from the bladder.

29. A method of indicating structural change of internal anatomical tissue as recited in claim 26 wherein said step of supplying includes the step of pressurizing the bladder with the fluidic substance to a predetermined pressure to cause the variable size passage to move to the open position in response to a specific structural change of the anatomical tissue.

30. A method of indicating structural change of internal anatomical tissue comprising the steps of providing a bladder having a variable size passage therein movable between a closed position sealing the bladder and an open position providing communication with the interior of the bladder;

providing an instrument for implanting the bladder in the body including a penetrating member having a distal end for penetrating the anatomical tissue and a syringe coupled with the penetrating member and containing a fluidic substance, the penetrating member including a channel extending from the syringe to the distal end of the penetrating member;

inserting the distal end of the penetrating member in the bladder through the variable size passage;

penetrating the anatomical tissue with the distal end of the penetrating member to position the bladder within the anatomical tissue;

squeezing the syringe to eject the fluidic substance from the syringe through the channel of the penetrating member into the interior of the bladder to pressurize the bladder to cause the variable size passage to be in the closed position preventing leakage of the fluidic substance from the bladder when the bladder is initially implanted in the body and to move to the open position to cause some of the fluidic substance to leak from the bladder when the bladder is stressed in response to structural change of the anatomical tissue; and withdrawing the distal end of the penetrating member from the bladder.

* * * * *